US006455608B1

(12) United States Patent
Jia et al.

(10) Patent No.: US 6,455,608 B1
(45) Date of Patent: Sep. 24, 2002

(54) DENTAL COMPOSITIONS COMPRISING DEGRADABLE POLYMERS AND METHODS OF MANUFACTURE THEREOF

(75) Inventors: Weitao Jia, Wallingford; Shuhua Jin, Cheshire; Samuel Jien-shek Huang, Bloomfield, all of CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/638,206

(22) Filed: Aug. 11, 2000

Related U.S. Application Data

(60) Provisional application No. 60/148,887, filed on Aug. 13, 1999.

(51) Int. Cl.$^7$ .......................... A61K 6/08; A61K 6/087; A61C 5/04
(52) U.S. Cl. ....................... 523/115; 523/116; 523/117; 433/228.1
(58) Field of Search ................................ 523/115, 116, 523/117; 106/35; 433/228.1

(56) References Cited

U.S. PATENT DOCUMENTS

| | | | |
|---|---|---|---|
| 3,925,895 A | | 12/1975 | Kliment et al. |
| 4,240,832 A | | 12/1980 | Jandourek |
| 4,343,608 A | | 8/1982 | Hodosh |
| 4,407,675 A | | 10/1983 | Hodosh |
| 4,657,592 A | | 4/1987 | Takubo |
| 4,732,943 A | | 3/1988 | Beech et al. |
| 4,931,096 A | | 6/1990 | Fujisawa et al. |
| 4,986,754 A | | 1/1991 | Chang et al. |
| 5,236,362 A | | 8/1993 | Cohen et al. |
| 5,380,772 A | | 1/1995 | Hasegawa et al. |
| 5,542,973 A | * | 8/1996 | Chow et al. |
| 5,624,976 A | | 4/1997 | Klee |
| 5,837,752 A | * | 11/1998 | Shastri et al. |
| 5,900,245 A | * | 5/1999 | Sawhney et al. |
| 5,915,970 A | | 6/1999 | Sicurelli, Jr. et al. |

FOREIGN PATENT DOCUMENTS

EP  0 438 255 A2  7/1991

OTHER PUBLICATIONS

I. Barakat, et al. entitled "Macromolecular Engineering of Polyactones and Polylactides. XV. Poly (D,L)–lactide Macromonomers as Precursors of Biocompatible Graft Copolymers and Bioerodible Gels" Aug. 1994, vol. 32, No. 11, pp. 2099–2110 in the Journal of Polymer Science.

Samuel J. Huang, et al. entitled Multicomponent Polymers of Poly(Lactic Acid) Macromonomers with Methacrylate Terminal and Copolmers of Poly(2–Hydroxyethyl Methacrylate) 1996, A33(5), pp. 571–584 in J.M.S.–Pure Appl. Chem.

John M. Onyari, et al. entitled "Multi–Component Comb Shaped and Networks Containing Poly(Lactic Acid)" in Polymer Material Science and Engineering, vol. 72, No. 1, p. 137.

Jose Luis Eguiburu, et al. entitled "Functionalization of poly(L–lactide) Macromonomers by ring–opening polymerization of L–lactide initiated with hydroxyethyl methacrylate–aluminium alkoxides" in Polymer, vol. 36, No. 1, p. 173 (1995).

Eguiburu, et al., "Graft Polymers for Biomedical Applications Prepared by Free Radical Polymerization of Poly(L–Lactide) Macromonomers with Vinyl and Acrylic Monomers", Polymer, GB, Elsevier Science Publishers, vol. 37, No. 16, (1996).

Database WPI, Section Ch, Week 199330, Darwent Publications Ltd., London, GB, Class A14 (1993).

Samuel J. Huang, et al, "Multicomponent Polymers of Poly(Latic Acid) Macromonomers with Methacrylate Terminal and Copolymers of Poly(2–Hydroxyethyl Methacrylate)", J.M.S.–Pure Appl. Chem., A33(5), pp. 571–584 (1996.

Yang–Kyoo Han, et al, "Synthesis and Characterization of Crosslinked Polymers for Biomedical Composites", J. Macromol. Sci.–Chem., A25(5–7), pp. 847–869 (1988).

* cited by examiner

*Primary Examiner*—Tae H. Yoon
(74) *Attorney, Agent, or Firm*—Cantor Colburn LLP

(57) ABSTRACT

Curable compositions comprising degradable macromonomers having one or more terminal acrylate or methacrylate functionality, a curing composition, and optionally one or more polymerizable acrylate or methacrylate comonomers. Degradable macromonomers are manufactured from cyclic monomers with compounds having acrylate or methacrylate functionality. Depending on their use, the degradable macromonomer compositions further comprise one or more organic or inorganic fillers, including a calcium-based compound and/or a radiopacity-imparting agent. The compositions are particularly suitable for root canal sealants, implants, and pulp capping materials.

26 Claims, No Drawings

DENTAL COMPOSITIONS COMPRISING DEGRADABLE POLYMERS AND METHODS OF MANUFACTURE THEREOF

CROSS-REFERENCE TO RELATED APPLICATIONS

This application claims priority to provisional application Ser. No. 60/148,887, filed Aug. 13, 1999, which is incorporated by reference herein in its entirety.

BACKGROUND OF THE INVENTION

1. Field of the Invention

This invention relates to dental compositions. In particular, this invention relates to dental compositions comprising degradable copolymers which are suitable for use as root canal sealants, root canal filling materials, implant materials, and in pulp capping.

2. Description of the Related Art

Endodontic therapy for a diseased or otherwise compromised tooth generally involves the dental practitioner accessing the root canal, debriding and disinfecting the root canal to clean and remove all of the soft tissue (the pulp) therein, and then enlarging the canal to remove irregularities or rough surfaces within the canal. A pre-formed "cone" or "point" is then inserted into the canal, and the cone is laterally or vertically condensed into the canal so that the point of the cone terminates at the apex of the canal. A commonly used cone material is gutta percha, which is a thermoplastic rubber. Because of the many irregularities which remain in the surface and shape of the canal even after treatment, it is difficult to achieve a satisfactory seal between the apex of the root canal and the cone without use of a root canal filler or sealant. Numerous sealants have been described, for example swellable hydrophilic acrylates and methacrylates such as 2-hydroxyethyl methacrylate (HEMA), as disclosed in U.S. Pat. No. 3,925,895 to Kliment et al. The monomers are mixed with polymerization initiator immediately prior to use and delivered to the root where polymerization occurs in situ. U.S. Pat. No. 4,986,754 discloses an injectable endodontic filling material comprising a mixture of balata or gutta percha with a liquid plasticizer. U.S. Pat. No. 4,449,938 discloses use of a two-component, room temperature setting organopolysiloxane compositions used for dental impression materials.

Despite these advances, the most commonly used root canal sealants remain compositions comprising a mixture of zinc oxide with eugenol (ZOE), and mixtures comprising calcium hydroxide. ZOE in particular is irritating to some patients, and has low adhesion to the walls of the root canal. Root canal sealants should be non-toxic, non-irritating, radiopaque, and have no or minimal shrinkage. They should also set within a reasonable period of time. They must be biologically compatible with tooth structure, and are preferably inert to moisture and to the pH conditions found in the mouth. Ideal preparations have low viscosity to facilitate insertion into the root canal, and even more preferably, are thixotropic. In the case of overflow of root canal sealant from the apex into the surrounding tissue or structure during a filling process, the overflowed excess should be desirably absorbed by the surrounding body tissue and cause tissue growth and recovery.

In contrast to endodontic procedures, in certain other dental procedures the pulp of the tooth is left intact. Where the pulp is exposed, a "pulp capping" compound is required which will preserve the vitality of the pulp. Pulp capping compounds must also be non-toxic, and cannot result in any irritation to the pulp. Ideal pulp capping compounds also allow for regrowth of the surrounding tissue and dentine. Calcium hydroxide-based pulp capping compounds are therefore common, as described in U.S. Pat. No. 3,047,400, and in U.S. Pat. No. 4,240,832, which discloses use of condensates of alkyl salicylates with aldehydes reacted with calcium hydroxide or calcium oxide. Despite these advances in the art, there remains a need for pulp capping materials which are biocompatible, non-toxic, and which have advantageous handling properties.

SUMMARY OF THE INVENTION

The above-discussed and other drawbacks and deficiencies of the prior art are overcome or alleviated by compositions comprising degradable macromonomers having biodegradable segments selected from the group consisting of poly(lactide), poly(glycolide), and poly(caprolactone), together with terminal acrylate or methacrylate functionality, a curing composition, and optionally a co-polymerizable acrylate or methacrylate monomer. Degradable macromonomers are manufactured by the polymerization of cyclic lactide, glycolide, or caprolactone in the presence of a compound having at least one active hydrogen and at least one acrylate or methacrylate functionality. Preferred active hydrogen containing acrylate or methacrylate compounds comprise 2-hydroxyethyl methacrylate, hydroxypolyethyl methacrylate, phenoxy-2-hydroxypropyl methacrylate, and the like. Preferred co-polymerizable acrylate or methacrylate monomers include diluent monomers such as 1,6-hexanediol dimethacrylate, triethylene glycol trimethacrylate and 2-hydroxyethyl methacrylate. Degradable macromonomers can also be manufactured by the esterification of hydroxyl-group(s) terminated macromonomers of the above-mentioned hydroxy acids with acrylic acid, methacrylic acid and their derivatives. Depending on their use, the degradable macromonomer compositions further comprise one or more organic or inorganic fillers and one or more radiopacity-imparting agents. A degradable macromonomer means degradation by means of hydrolysis and/or biodegredation.

The present compositions are expected to be biocompatible and biodegradable, which advantageously allows for tissue regrowth. The degradable macromonomer compositions therefore find particular utility as root canal sealants, implant materials, and as pulp capping compositions. The above-discussed and other features and advantages of the present invention will be appreciated and understood by those skilled in the art from the following detailed description.

DETAILED DESCRIPTION OF THE PREFERRED EMBODIMENTS

The present compositions comprise degradable macromonomers having terminal acrylate or methacrylate groups, a curing agent, and optionally one or more co-polymerizable acrylate or methacrylate monomer. Depending on their use, the degradable macromonomer compositions further comprise optional organic or inorganic filler and a radiopacity-imparting agent.

Degradable macromonomers having terminal acrylate or methacrylate groups are obtained by the polymerization and copolymerization of lactide, glycolide or caprolactone in the presence of a compound having at least one active hydrogen, such as an amine or a hydroxyl group, and at least one acrylate or methacrylate functionality. Such compounds include but are not limited to hydroxyalkyl acrylates and methacrylates wherein the alkyl group has from 1 to 12 carbons, such as 2-hydroxyethyl methacrylate (HEMA), 2-hydroxyethyl acrylate, diethylene glycol monomethacrylate, diethylene glycol monoacrylate, hydroxypropyl methacrylate, hydroxypropyl acrylate, tetraethyleneglycol monomethacrylate, tetraethyleneglycol monoacrylate, pentaethyleneglycol monomethacrylate, pentaethyleneglycol monoacrylate, dipropyleneglycol monomethacrylate, dipropyleneglycol monoacrylate, hydroxy polyethyl methacrylates, phenoxyhydroxyphenyl methacrylate and the like. HEMA is preferred. Degradable macromonomers having terminal acrylate or methacrylate groups can also be manufactured by the esterification of hydroxyl-group(s) terminated macromonomers of the above mentioned hydroxy acids with acrylic acid, methacrylic acid and their derivatives.

Lactide is the cyclic dimer of lactic acid, and is available as both L-lactide ((3S)-cis-3,6-dimethyl-1,4-dioxane-2,5-dione) and D,L-lactide (3,6-dimethyl-1,4-dioxane-2,5-dione). Polymerization of lactide with HEMA, for example, yields a poly(lactide-HEMA) (hereinafter PLAMA) macromonomer having the following structure (I), wherein m=1, n≧1, and G is hydroxyl, or acrylate or methacrylate containing terminal non-polymerizable esters:

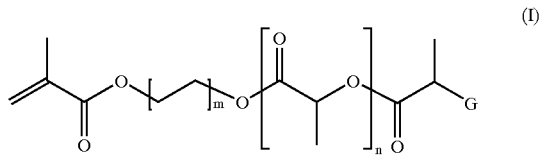

(I)

Synthesis of suitable poly(lactic acid) macromonomers having terminal acrylate or methacrylate groups is described by S. J. Huang and J. M. Onyari, in "Multicomponent Polymers of Poly(Lactic) Acid Macromonomers With Methacrylate Terminal and Copolymers of Poly(2-Hydroxyethyl Methacrylate)", in *Journal of Macromolecular Science—Pure and Applied Chemistry*, Volume A33, No. 5, pp. 571–584 (1996); by S. J. Huang and J. M. Onyari in *Polymer Material Science and Engineering*, Volume 72, No. 1, p. 137; by I. Barakat, P. Dubois, R. Jerome, P. Teyssie, and E. Goethais, in *Journal of Polymer Science, Polymer Chem. Ed.*, Vol. 32, p. 2099 (1994); and by J. L. Eguiburu, M. J. F. Berridi, and J. San Romain, *Polymer*, Vol. 36, No. 1, p. 173 (1995). All of the preceding references are incorporated herein in their entirety.

Polymerization of glycolide with HEMA, for example, yields a poly(glycolide-HEMA) macromonomer having the following structure (II), wherein m=1, n≧1, and G is hydroxyl, or acrylate or methacrylate containing terminal non-polymerizable esters:

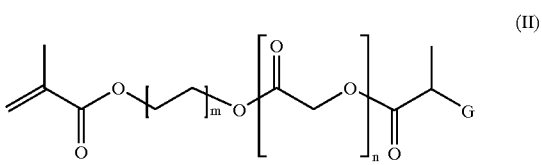

(II)

Polymerization of caprolactone with HEMA yields a poly(caprolactone-HEMA) macromonomer having the following structure (III), wherein m=1, n≧1, and G is hydroxyl, or acrylate or methacrylate containing terminal non-polymerizable esters:

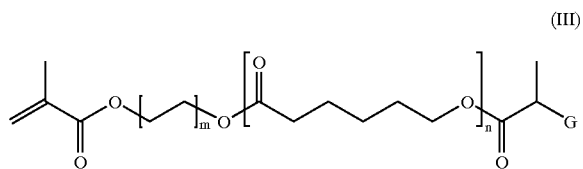

(III)

Copolymerization of a mixture of lactide, glycolide, and caprolactone with HEMA yields a macromonomer having the following structure (IV), wherein m=1, $n_1$, $n_2$, and $n_3$ are each independently one or greater, and G is hydroxyl, or acrylate or methacrylate containing terminal non-polymerizable esters:

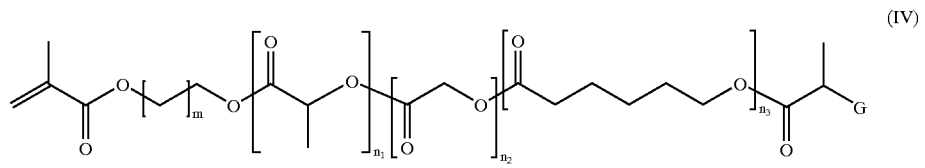

(IV)

Copolymerization of a mixture of lactide and glycolide with HEMA yields PGLMA, a macromonomer having the following structure (V), wherein m=1, $n_1$ and $n_2$ are each independently one or greater, and G is hydroxyl, or acrylate or methacrylate containing terminal non-polymerizable esters:

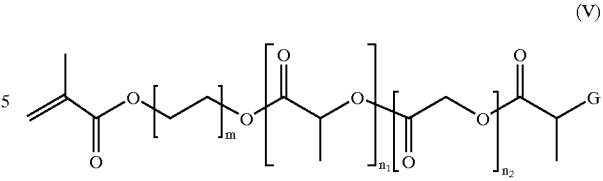

(V)

Another preferred degradable macromonomer is commercially available 2-(caprolactone)ethyl methacrylate (CLMA).

The optional co-polymerizable acrylate or methacrylate monomer is selected from those known for use as dental materials, and is typically present in amounts in the range from 0% to 95% by weight of the total composition. Multi-functional, diluent, i.e., low viscosity monomers, are preferred. Such monomers provide crosslinking and allow the viscosity of the composition to be adjusted for easy delivery to the root canal, while maintaining advantageous physical properties of the polymerized product. Exemplary diluent monomers include but are not limited to liquid dimethacrylate, trimethacrylate, or higher monomers, such as glycerol dimethacrylate, ethylene glycol dimethacrylate, tri(ethylene glycol) dimethacrylate (hereinafter TEGDMA), tetra(methylene glycol) dimethacrylate, trimethylolpropane trimethacrylate, 1,6-hexanediol dimethacrylate (hereinafter HDDMA), 2-hydroxyethyl acrylate and 1,3-butanediol dimethacrylate. These monomers are characterized by relatively low molecular weight (e.g., 400 or less) and low viscosity.

Other monomers may be used in combination with the foregoing co-polymerizable monomers, including viscous methacrylate-based monomers such as 2,2'-bis [4-(2-hydroxy-3-methacryloxypropoxy)phenyl]propane (hereinafter "Bis-GMA") as described in U.S. Pat. No. 3,066,112 to Bowen, which is incorporated by reference herein, or non-hydroxylated resins such as urethane dimethacrylate (hereinafter "UDMA"), or alkylated hydroxyl-containing resins such as ethoxylated bisphenol A dimethacrylate (hereinafter "EBPDMA"). EBPDMA in particular is effective in reducing the water sorption of the final product. A combination of the aforementioned resins may also be used.

The acrylate- or methacrylate-terminated degradable macromonomer compositions further comprise a curing composition. Suitable curing compositions for use with acrylate or methacrylate-based monomers are known in the art, and may be light cure, heat-cure, or a self cure system, or a combination thereof. Use of a dual-cure system and optional accelerators yields a composition that cures evenly and completely.

The light cure system is selected from known light-activated polymerization initiators, including but not being limited to benzil, benzoin, benzoin methyl ether, DL-camphorquinone (CQ) and benzil diketones. Either UV-activated cure or visible light-activated cure (approx. 230 to 750 nm) is acceptable. The amount of photoinitiator is selected according to the curing rate desired. A minimally catalytically effective amount is generally about 0.01% by weight of the polymeric components, and will lead to a slower cure. Faster rates of cure are achieved with amounts of catalyst in the range from greater than about 0.01% to about 5% by weight of the polymeric component.

The heat-cure initiator is selected from those known in the art such as benzoyl peroxide, lauroyl peroxide, dicumyl peroxide, 1,1'-azobis(cyclohexanecarbonitrile), or other free radical initiators. The amount of free-radical catalyst is selected according to the curing rate desired. A minimally catalytically effective amount is generally about 0.5% by weight of the polymeric components, and will lead to a slower cure. Faster rates of cure are achieved with amounts of catalyst in the range from above about 0.5% to about 6.0% by weight of the polymeric component. In one embodiment, the heat-cure initiator is activated by the heat of reaction generated by the light-activated polymerization process. This embodiment is particularly advantageous because the composition may be supplied to the practitioner pre-mixed, that is, as a single-component mixture ready for application to the site of restoration. In a particularly preferred embodiment, the composition is supplied in pre-packaged syringes, compules, or cartridges.

Optional cure accelerators may further be included in the light curing composition. Polymerization accelerators are the various organic tertiary amines well known in the art. In visible light compositions, the tertiary amines are generally acrylate derivatives such as 2-(diethylamino)ethyl methacrylate (commonly known as "DEAEMA") and 2-(dimethylamino)ethyl methacrylate, in amounts in the range from about 0.05 to about 0.5 percent by weight of the polymeric composition.

Alternatively, the composition may be formulated with as a self-curing two-part system which is stored separately and mixed in equal amounts prior to use to initiate cure. Self-cure systems comprise an initiator such as a peroxide in one part, and an accelerator such as a tertiary amine, generally tertiary aromatic amines such as ethyl 4-(dimethylamino) benzoate (commonly known as "EDMAB"), 2-[4-(dimethylamino)phenyl]ethanol, N,N-dimethyl-p-toluidine (DMPT), bis(hydroxyethyl)-p-toluidine, and triethanolamine in a second part. Such accelerators are generally present in the range from about 0.5 to about 4.0% by weight of the polymeric component. Another self-curing system comprises of thiourea or thiourea derivatives as the reductant and hydrogen peroxide as the oxidant, as described in U.S. Pat. No. 3,991,008. Both parts generally comprise the degradable macromonomer, co-polymerizable acrylate or methacrylate monomer, and filler in various amounts, with the initiator, for example dibenzoyl peroxide (BPO), being stored in one part, and the accelerator, e.g., N,N-dihydroxyethyl-p-toluidine being stored in another part. Equal amounts of part A and Part B are mixed by the dentist or technician immediately prior to use.

The acrylate- or methacrylate-terminated degradable macromonomer compositions further preferably comprise a filler system, wherein the filler comprises at least 5%, preferably at least 25%, and most preferably at least about 50% by weight of an inorganic calcium-containing compound, for example, calcium hydroxide, calcium phosphates, tricalcium phosphate, or calcium oxide, based on the total composition.

Other fillers which may be used in combination with the calcium-based compound include inorganic and organic particulates and fibrous fillers known in the art, such as particulate poly(lactide), poly(glycolide), poly(lactide-co-glycolide) or poly(methacrylate), or particulate or fibrous silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania. Particularly suitable fillers are those having a particle size ranging from about 0.1–5.0 micron, with a fumed silica of 0.001 to about 0.07 microns and prepared by a series of milling steps comprising wet milling in an aqueous medium, surface etch milling and silanizing milling in a silane solution. Some of the aforementioned inorganic filling materials are disclosed in commonly-assigned U.S. Pat. Nos. 4,544,359 and 4,547,531 to Waknine, the pertinent portions of which are incorporated herein by reference.

It is also within the scope of the present invention that certain radiopaque/high refractive index materials, such as apatites, may be used as filler materials. Suitable high refractive index filler materials include, but are not limited to, high refractive index silica glass fillers, calcium silicate based fillers such as apatites, hydroxyapatites or modified hydroxyapatite compositions. Alternatively, inert, non-toxic radiopaque materials such as barium sulfate and bismuth subcarbonate may be included.

The compositions may further comprise anti-oxidants, for example BHT (2,6-di-tert-butyl-4-methylphenol) or hydroquinone methyl ether in amounts in the range from about 0.1 to about 0.3% by weight of the polymerizable components; ultraviolet stabilizers to prevent discoloration, for example benzophenones such as 2-hydroxy-4-methoxybenzophenone, benzotriazoles, such as 2-(2'-hydroxy-5'-methylphenyl)benzotriazole, 2-(2-hydroxy-5-tert-octylphenyl)benzotriazole (available under the trade name UV-54 from American Cyanamid Company) and other derivatives thereof; fluorescent whitening agents such as 2,5-bis(5-tert-butyl-2-benzoxazole) thiophene (available under the trade name UV-OB); trace amounts of FDA and FDC approved dyes, for example carbon black, yellow No. 5, yellow No. 6, and the like; and other additives known in the art.

Medicaments may also be included in the compositions in an amount effective to prevent infection and/or inflammation, generally from about 1% to about 10% by weight of the total composition. Suitable medicaments include but are not limited to pain relieving agents such as Novocaine (procaine hydrochloride), Benzocain (ethyl aminobenzoate), ascorbic acid, butacaine sulfonate, dibutacaine hydrochloride, anti-biotics such as sulfadiazine, procaine penicillin, aureomycin, streptomycin, terramycin, chloramphenicol, butabarbital, diethyl stilbestrol, and anti-inflammation agents such as p-aminosalicylic acid, aspirin, and the like.

Another preferred embodiment of the present invention is a method of forming a dental restorative comprising preparing a site to be restored in a tooth; and applying a composition comprising (a) at least one degradable macromonomer having terminal acrylate or methacrylate groups; (b) a curing composition; and (c) optionally one or more co-polymerizable acrylate or methacrylate monomers.

The present invention is preferable to the currently available art for root canal sealants, implant materials, and pulp capping compositions because the compositions of the present invention are expected to be non-toxic, biodegradable and biocompatible. These properties are ideal for tissue regrowth in the surrounding tissue and dentine when the compositions are used in pulp capping procedures or root canal procedures. Also, the present compositions have low shrinkage, which is required for use as root canal sealants.

The invention is further illustrated by the following non-limiting Examples. Synthesis of PLAMA was in accordance with Huang (1996).

EXAMPLE 1

Degradation of Cured PLAMA/TEGDMA Compositions

The degradation of cured PLAMA/TEGDMA for varying quantities of PLAMA was studied in a buffer solution of pH 7 over time. The curing of PLAMA/TEGDMA was performed in light box for 2 minutes using a curing composition comprising 0.2% by weight CQ and 0.2% by weight DEAEMA. PLAMA and TEGDMA were mixed to give various weight percents (based on the total resin composition) of PLAMA in accordance with Table 1 below. The amount of TEGDMA or other suitable crosslinker/diluent resin can also be varied according to the viscosity and molecular weight of the PLAMA used. The samples were prepared as 1 mm thick disks, weighed to determine the original weight, and immersed in pH 7 buffer and then stored at 37° C. The samples were removed from the solution monthly, oven-dried, and weighed to determine degradation, as reflected by weight loss. Weight loss is calculated by subtracting the dried weight from the original weight, and dividing that amount by the original weight. Results are shown in Table 1.

TABLE 1

| PLAMA (wt. %) | Weight Loss (wt. %) | | | |
|---|---|---|---|---|
| | 0.5 month | 1 month | 2 month | 3 month |
| 25 | 4.2 | 10.8 | 21 | 24 |
| 50 | 3.9 | 23.0 | 29 | 31 |
| 55 | 6.8 | 23.5 | 34 | 35 |
| 60 | 5.0 | 29.0 | 44 | 46 |
| 75 | 11.5 | 41.0 | 56 | 59 |
| 90 | 17.7 | 56.0 | 69 | 73 |
| Control* | −0.05 | −0.04 | 0.01 | 0.02 |

*BIS GMA/UDMA/HDDMA (33/34/33) resin by weight with 0% PLAMA

As shown in Table 1, degradation of the samples is related to the weight percent of PLASMA used to prepare the samples, such that degradation of the samples increases with the increasing quantities of PLAMA relative to TEGMA. When no PLAMA is present, no degradation is observed.

EXAMPLE 2

Shrinkage of Copolymerized PLAMA/TEGDMA

Shrinkage of PLAMA/TEGDMA resins was measured by a dilatometer (ADA Health Foundation, Maryland, USA). The measurement was performed on samples prepared by mixing 20 vol % of fumed silica (OX-50 from Degussa) into resins copolymerized using varying quantities of PLAMA. Results are shown in Table 2.

TABLE 2

| PLAMA (wt. %) | Shrinkage (% by volume) |
|---|---|
| 60 | 5.59 |
| 75 | 3.94 |
| 90 | 2.92 |
| Control* | 6.14 |

*BIS GMA/UDMA/HDDMA (33/34/33) resin by weight

Shrinkage is also related to weight percent of PLAMA present, such that the higher the ratio of PLAMA used, the lower the shrinkage observed. Lower shrinkage is essential in root canal sealing materials.

EXAMPLE 3

Self-cure of PLAMA/TEGDMA Resins

Self-curing formulations of 70/30 by weight PLAMA/TEGDMA compositions comprising organic and/or inorganic fillers were studied, using a two-part formulation. The inorganic fillers are $BaSO_4$ and tricalcium phosphate (TCP). An exemplary formula is shown in Table 3. When equal parts of the base and catalyst formulation are mixed, this formula has a viscosity suitable for root canal sealants and for pulp capping.

TABLE 3

Exemplary Formula of Self-Cured PLAMA/TEGDMA

| Component | PLAMA/<br>TEGDMA<br>(70/30 by wt.) | BaSO$_4$ | TCP | BHT | DMPT | BPO |
|---|---|---|---|---|---|---|
| Base | 60 g | 20 g | 20 g | 300 ppm | 1 g | — |
| Catalyst | 60 g | 20 g | 20 g | 600 ppm | — | 2 g |

Gel time=7 min, 30 sec.
Setting time=10 min, 20 sec.

EXAMPLE 4

Degradation of Example 3

Example 3 above was tested for degradation using the method of Example 1. Results are shown in Table 4.

TABLE 4

| Time (month) | 0.5 | 1 | 2 | 3 |
|---|---|---|---|---|
| Degradation (wt. %) | 6.4 | 13 | 22 | 26.4 |

EXAMPLE 5

2-(Caprolactone)ethyl methacrylate (CLMA) was used as the base resin. PGLMA/HDDMA in the ratio of 70/30 was used as the catalyst resin. An exemplary formula is shown in Table 5. When equal parts of the base and catalyst formulation are mixed, this formula has a viscosity suitable for root canal sealants and for pulp capping.

TABLE 5

| Component | CLMA PLGMA/HDDMA | BaSO$_4$ | TCP | Ca(OH)$_2$ | BHT | BPO | DMPT |
|---|---|---|---|---|---|---|---|
| Base | 50 g | 20 g | 20 g | 10 g | 0.025 g | — | 0.75 g |
| Catalyst | 60 g | 20 g | 20 g | — | 0.60 g | 1.8 g | — |

Gel time=12 min, 30 sec.
Setting time=16 min.

EXAMPLE 6

Degradation of Example 5

Example 5 was tested for degradation using the method of Example 1. Results are shown in Table 6.

TABLE 6

| Time (day) | 7 | 15 | 21 | 30 |
|---|---|---|---|---|
| Degradation (wt. %) | 3.7 | 4.4 | 5.1 | 6.4 |

For regular non-degradable cement (Cement C&B, Jeneric/Pentron), the weight loss in a month is about 0.3%.

EXAMPLE 7

The monomers used in this formulation are 70/30 PLAMA/TEGMA.

TABLE 7

| Component | 70/30 PLAMA/TEGMA | BaSO$_4$ | TCP | BHT | Acetyl thiourea | Cumene hydroperoxide |
|---|---|---|---|---|---|---|
| Base | 60 g | 20 g | 20 g | 0.06 g | 4 g | — |
| Catalyst | 60 g | 20 g | 20 g | 0.06 g | — | 4 g |

Gel time=7 min, 45 sec.
Setting time=11 min, 45 sec.

EXAMPLE 8

100 grams of PLAMA with an additional 0.2 parts CQ and 0.2 parts DEAMA were mixed. The resin composition was prepared as 1 mm thick disc and cured for 2 minutes in a light box, giving a hardened solid. This composition may be used as a degradable surface sealant.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of forming a dental restoration comprising:
   preparing a site to be restored in a tooth; and
   applying a composition comprising
   (a) at least one degradable macromonomer having terminal acrylate or methacrylate groups, wherein the degradable macromonomer having terminal acrylate or methacrylate groups is the reaction product of lactide, glycolide, caprolactone, or a mixture thereof with a compound having at least one active hydrogen and at least one acrylate or methacrylate functionality;
   (b) a curing composition; and
   (c) optionally one or more co-polymerizable acrylate or methacrylate monomers.

2. The method of claim 1, wherein the active hydrogen is a hydroxyl hydrogen.

3. The method of claim 1, wherein the compound is selected from the group consisting of hydroxyalkyl acrylates and methacrylates wherein the alkyl group has from 1 to 12 carbons, and mixtures comprising at least one of the foregoing.

4. The method of claim 3, wherein the compound is selected from the group consisting of 2-hydroxyethyl methacrylate, 2-hydroxyethyl acrylate, diethylene glycol monomethacrylate, diethylene glycol monoacrylate, hydroxypropyl methacrylate, hydroxypropyl acrylate, tetraethyleneglycol monomethacrylate, tetraethyleneglycol monoacrylate, pentaethyleneglycol methacrylate, hydroxypolyethyl methacrylate, pentaethyleneglycol monoacrylate, dipropyleneglycol monomethacrylate, dipropyleneglycol monoacrylate, phenoxyhydroxyphenyl methacrylate, and mixtures comprising at least one of the foregoing.

5. The method of claim 1, wherein the degradable macromonomer having terminal acrylate or methacrylate groups is 2-(caprolactone)ethyl methacrylate.

6. The method of claim 1, wherein the co-polymerizable acrylate or methacrylate monomer is a diluent monomer present in an amount effective to provide delivery to the root canal using an applicator.

7. The method of claim 6, wherein the diluent monomer is selected from the group consisting of liquid dimethacrylate, trimethacrylate, glycerol dimethacrylate, ethylene glycol dimethacrylate, tri(ethylene glycol) dimethacrylate, tetra(methylene glycol)dimethacrylate, trimethylolpropane trimethacrylate, 1,6-hexanediol dimethacrylate, 2-hydroxyethyl acrylate, and 1,3-butanediol dimethacrylate.

8. The method of claim 1, wherein the curing composition is selected from the group consisting of light-activated polymerization initiators, heat-cure initiators, a self-curing two-part system, and combinations thereof.

9. The method of claim 1, wherein the curing composition is a self-curing two-part system mixed prior to use comprising an initiator in one part and an accelerator in a second part whereby the two parts contain equal or various amounts of the degradable macromonomer and co-polymerizable acrylate or methacrylate monomer.

10. The method of claim 1, further comprising a filler composition.

11. The method of claim 4, wherein the compound is 2-hydroxyethyl methacrylate.

12. The method of claim 1, wherein the co-polymerizable acrylate or methacrylate monomer is present in amounts in a range from about 0% to 95% by weight of the total composition.

13. The method of claim 6, wherein the diluent monomer is used in combination with an acrylate selected from the group consisting of viscous methacrylate-based monomers, 2,2'-bis[4-(2-hydroxy-3-methacryloxypropoxy)phenyl] propane, urethane dimethacrylate and ethoxylated bisphenol A dimethacrylate.

14. The method of claim 8, wherein the light-activated polymerization initiators are selected from the group consisting of benzil, benzoin, benzoin methyl ether, DL-camphorquinone, and benzil diketones.

15. The method of claim 8, wherein the light-activated polymerization initiators are used in combination with cure accelerators.

16. The method of claim 15, wherein the cure accelerators are tertiary amines.

17. The method of claim 8, wherein the heat-cure initiators are free radical initiators.

18. The method of claim 8, wherein the heat-cure initiators are selected from the group consisting of benzoyl peroxide, lauroyl peroxide, dicumyl peroxide, and 1,1'-azobis(cyclohexanecarbonitrile).

19. The method of claim 8, wherein the heat-cure initiators are activated by the beat of reaction generated by the light-activated polymerization process.

20. The method of claim 19, wherein the composition is pre-mixed as a single-component mixture and optionally supplied in syringes, compules, or cartridges.

21. The method of claim 10, wherein the filler is selected from the group consisting of inorganic calcium compounds, calcium phosphates, calcium hydroxide, calcium oxide, tricalcium phosphate, and combinations thereof.

22. The method of claim 21, wherein the filler composition further comprises other fillers selected from the group consisting of poly(lactide), poly(glycolide), poly(lactide-co-glycolide), poly(methacrylate), silica, fumed silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania.

23. The method of claim 10, wherein the filler is selected from the group consisting of radiopaque material and high refractive index material.

24. The method of claim 23, wherein the radiopaque material is selected from the group consisting of barium sulfate and bismuth subcarbonate.

25. The method of claim 23, wherein the high refractive index material is selected from the group consisting of high refractive index silica glass fillers, apatites, hydroxyapatites, and modified hydroxyapatite compositions.

26. The method of claim 1, optionally containing additives selected from the group consisting of dyes, ultraviolet stabilizers, fluorescent whitening agents, anti-oxidants, and medicaments.

* * * * *